United States Patent [19]

Bowes et al.

[11] Patent Number: 4,579,993

[45] Date of Patent: Apr. 1, 1986

[54] CATALYST FOR METHANOL CONVERSION BY A COMBINATION OF STEAMING AND ACID-EXTRACTION

[75] Inventors: Emmerson Bowes, Hopewell; Clarence D. Chang, Princeton; Richard F. Socha, Trenton, all of N.J.

[73] Assignee: Mobil Oil Corporation, New York, N.Y.

[21] Appl. No.: 643,345

[22] Filed: Aug. 22, 1984

[51] Int. Cl.[4] .............................................. C07C 1/00
[52] U.S. Cl. .................................... 585/640; 585/733
[58] Field of Search ................... 585/640, 733; 502/85

[56] References Cited

U.S. PATENT DOCUMENTS

| | | |
|---|---|---|
| 4,076,842 | 2/1978 | Plank et al. ......................... 585/640 |
| 4,429,176 | 1/1984 | Chester et al. ...................... 585/640 |
| 4,440,958 | 4/1984 | Gregory et al. ...................... 502/85 |
| 4,447,669 | 5/1984 | Hamon et al. ...................... 585/640 |
| 4,480,145 | 10/1984 | Brennan et al. ..................... 585/640 |

*Primary Examiner*—William R. Dixon, Jr.
*Assistant Examiner*—Cynthia A. Prezlock
*Attorney, Agent, or Firm*—Alexander J. McKillop; Michael G. Gilman; James F. Powers, Jr.

[57] ABSTRACT

An improved catalyst for methanol conversion having enhanced stability is obtained by extruding a zeolite having a silica-to-alumina ratio of at least 12 and a Constraint Index within the approximate range of 1 to 12 with a silica matrix and thereafter subjecting the extrudate to both steaming and acid-extraction in order to enhance the stability thereof.

9 Claims, No Drawings

CATALYST FOR METHANOL CONVERSION BY A COMBINATION OF STEAMING AND ACID-EXTRACTION

BACKGROUND OF THE INVENTION

1. Field of the Invention

This invention is concerned with a method of increasing the catalytic cycle length in methanol conversion catalysts by a combination of steaming and acid extraction. The acid-extraction step in accordance with the novel process of this invention requires the use of a crystalline aluminosilicate zeolite in a silica matrix.

2. Description of the Prior Art

The conversion of lower alcohols, including methanol, to various products such as gasoline, olefins, and/or distillates is an important area of technology which has been described in the patent and technical literature. The particularly advantageous catalysts which are utilized in the conversion of methanol are a special class of crystalline aluminosilicate zeolites having a silica-to-alumina ratio greater than 12 and a Constraint Index within the approximate range of 1 to 12. A typical material of this type is zeolite ZSM-5. There are many patents and publications which describe the conversion of methanol to hydrocarbons such as gasoline, olefins and/or distillates over said special zeolites including U.S. Pat. Nos. 3,931,349; 3,969,426; 3,899,544; 3,894,104; 3,904,916; 3,894,102; 4,025,576; 4,374,295; and 4,083,889; the disclosures of which are herein incorporated by reference. It is also known in the art that steaming under certain circumstances can enhance the activity of acid catalyzed reactions and such is disclosed in U.S. Pat. No. 4,326,994. It is also known that steaming can enhance the stability of zeolite catalysts for various acid catalyzed reactions as well as methanol conversion and such is disclosed and claimed in U.S. Pat. No. 4,429,176. It is also known in the art that treatment with phosphorus and/or steam can extend the life of an isomerization catalyst such as disclosed and claimed in U.S. Pat. No. 4,423,266.

SUMMARY OF THE INVENTION

It has been discovered that pretreatment of a special class of zeolite catalysts incorporated in a silica matrices by a combination of both steaming and acid-extraction increases the cycle life of the catalyst over that which would be obtained if either acid-extraction itself or steaming itself were carried out. In other words, for reasons which are not completely understood, the combination of acid-extraction and steaming enhances the stability of a special class of crystalline aluminosilicate zeolites, particularly when said zeolite is combined, dispersed, or otherwise incorporated into a silica matrix.

DESCRIPTION OF THE SPECIFIC EMBODIMENTS

The crystalline zeolites utilized herein are members of a particular class of zeolitic materials which exhibit unusual properties. Although these zeolites have unusually low alumina contents, i.e. high silica-to-alumina mole ratios, they are very active even when the silica-to-alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this special class of zeolites is that it provides a selective constrained access to and egress from the intracrystalline free space by virtue of having an effective pore size intermediate between the small pore Linde A and the large pore Linde X, i.e., the pore windows of the structure are of about a size such as would be provided by 10-membered rings of silicon atoms interconnected by oxygen atoms. It is to be understood, of course, that these rings are formed by the regular disposition of the tetrahedra making up the anionic framework of the crystalline zeolite, the oxygen atoms themselves being bonded to the silicon (or aluminum, etc.) atoms at the centers of the tetrahedra.

The silica-to-alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica-to-alumina ratio of at least 12 are useful, it is preferred in some applications to use zeolites having higher silica/alumina ratios of at least about 30. In addition, zeolites as otherwise characterized herein but which are substantially free of aluminum, i.e. having silica-to-alumina mole ratios of 1600 and higher, are found to be useful and even preferable in some instances. Such "high silica" zeolites are intended to be included within this description. The particular class of zeolites, after activation, acquire an intracrystalline sorption capacity for normal hexane which is greater than that for water, i.e., they exhibit "hydrophobic" properties. This hydrophobic character can be used to advantage in some applications.

The particular class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedures. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10% to 60% for most zeolite samples and represents preferred conditions, it may occasionally be necessary to use somewhat more severe conditions for samples of very low activity, such as those having an exceptionally high silica-to-alumina mole ratio. In those instances, a temperature of up to about 540° C. and a liquid hourly space velocity of less than one, such as 0.1 or less, can be employed in order to achieve a minimum total conversion of about 10%.

$$\text{Constraint Index} = \frac{\log_{10} (\text{fraction of hexane remaining})}{\log_{10} (\text{fraction of 3-methylpentane remaining})}$$

The Constraint Index approximates the ratio of the cracking rate constant for the two hydrocarbons. Zeolites suitable for the present invention are those having a Constraint Index of 1 to 12. Constraint Index (CI) values for some typical materials are:

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the Constraint Index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined special class of highly siliceous zeolites are those zeolites which, when tested under two or more sets of conditions within the above-specified ranges of temperature and conversion, produce a value of the Constraint Index slightly less than 1, e.g., 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant zeolite definition whether or not the same identical zeolite, when tested under other of the defined conditions may give a Constraint Index value outside of the range of 1 to 12.

The particular class of zeolites defined herein is exemplified by ZSM-5, ZSM-11, ZSM-12, ZSM-23, ZSM-35, ZSM-38, ZSM-48, and other similar materials.

ZSM-5 is described in greater detail in U.S. Pat. Nos. 3,702,886 and 3,941,871. The entire descriptions contained within those patents, particularly the X-ray diffraction pattern of therein disclosed ZSM-5, are incorporated herein by reference.

ZSM-11 is described in U.S. Pat. No. 3,709,979. That description and, in particular, the X-ray diffraction pattern of said ZSM-11 is incorporated herein by reference.

ZSM-12 is described in U.S. Pat. No. 3,832,449. That description and, in particular, the X-ray diffraction pattern disclosed therein is incorporated herein by reference.

ZSM-23 is described in U.S. Pat. No. 4,076,842. The entire content thereof, particularly the specification of the X-ray diffraction pattern of the disclosed catalyst, is incorporated herein by reference.

ZSM-35 is described in U.S. Pat. No. 4,016,245. The description of that catalyst, and particularly the X-ray diffraction pattern thereof, is incorporated herein by reference.

ZSM-38 is more particularly described in U.S. Pat. No. 4,046,859. The description of that catalyst, and particularly the specified X-ray diffraction pattern thereof, is incorporated herein by reference.

ZSM-48 is more particularly described in U.S. Pat. No. 4,397,827 and in European patent application Ser. No. 80 300,463, published Sept. 3, 1980, as Publication No. 0015132, the content of which is incorporated herein by reference.

It is to be understood that by incorporating by reference the foregoing patents to describe examples of specific members of the zeolite class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38, and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica-to-alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the intenstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | 0.28 | 1.7 |
| ZSM-5, −11 | 0.29 | 1.79 |
| ZSM-12 | — | 1.8 |
| ZSM-23 | — | 2.0 |
| Dachiardite | 0.32 | 1.72 |
| L | 0.32 | 1.61 |
| Clinoptilolite | 0.34 | 1.71 |
| Laumontite | 0.34 | 1.77 |
| ZSM-4 (Omega) | 0.38 | 1.65 |
| Heulandite | 0.39 | 1.69 |
| P | 0.41 | 1.57 |
| Offretite | 0.40 | 1.55 |
| Levynite | 0.40 | 1.54 |
| Erionite | 0.35 | 1.51 |
| Gmelinite | 0.44 | 1.46 |
| Chabazite | 0.47 | 1.45 |
| A | 0.5 | 1.3 |
| Y | 0.48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the preferred hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

It has long been recognized in the art that silica is a desirable matrix and that it possessed advantages over alumina with regard to certain catalytic reactions. In this connection, U.S. Pat. No. 4,013,732 specifically discloses ZSM-5 with a silica matrix at column 7. Further, until very recently, it was not possible to prepare an extrudate of a silica matrix with a special class of crystalline aluminosilicate zeolites of this invention due to the fact that extrusion created problems which resulted in poor mechanical properties.

In copending patent application entitled EXTRUSION OF SILICA-RICH SOLIDS, Ser. No. 628,680, filed July 6, 1984, in the name of Emmerson Bowes a process is disclosed for extruding silica-rich solids which comprises mixing the same with water and an alkali metal base or basic salt followed by mulling and extruding with the amount of water added sufficient to provide a total solids content of from 25 to 75 weight percent. The resulting product has a crush strength of at least 4 pounds for a ⅛th of an inch length having a diameter of 1/16th of an inch.

The entire disclosure of said copending application is herein incorporated by reference.

In accordance with the novel process of this invention, a zeolite previously described such as ZSM-5 is mixed with water and an alkali metal base, such as sodium hydroxide, wherein the amount of water added is sufficient to provide a total solids content of 25 to 75 weight percent and the alkali metal compound is added in an amount of 0.5 to 10 weight percent on a dry basis based on the total solids and calculated as sodium hydroxide equivalent followed by mulling and extruding through any conventional extruder. The extrudate is then subjected to a combination of steaming and acid-extraction in order to enhance the stability of a catalyst. It is pointed out that the order of steaming and acid-extraction is not critical and one can be carried out prior to the other.

Steaming is generally carried out by contacting the extrudate with steam at a temperature of from 400° C. to 600° C. for 2 to 100 hours. Steam can either be a 100% steam or diluted with air or inert gas.

The acid-extraction is carried out by contacting the extrudate either before or after steaming with a strong acid such as nitric acid, hydrochloric acid, sulfuric acid, etc. at 15° C. to 100° C. for 0.5 to 10 hours. The strength of the acid is not narrowly critical and can vary from 0.1 to 10.0 normal. Following the treatment with both steam and acid, the resulting zeolite extrudate is usually washed with water, dried and calcined at elevated temperatures ranging from 400° C. to 600° C. for a period of time ranging from 0.5 to 16 hours.

As indicated earlier, methanol conversion with the ZSM-5 catalyst of this invention is extremely known in the art and is carried out at elevated temperatures and pressures ranging from atmospheric to 500 psig at a space velocity ranging from 0.5 to 4 depending upon whether olefins or aromatics are the desired product.

The following example will illustrate the novel process of this invention.

EXAMPLE 1

Sixty-five (65) weight percent of ZSM-5 and 35 weight percent of silica were bound together by first mulling the zeolite as-synthesized with silica (Hi-Sil 233) while adding water containing 3% by weight of sodium hydroxide calculated on the final weight of total solids and extruding through a 1/16th of an inch die plate. The material was then calcined by heating the same in nitrogen at 538° C. for 3 hours, ammonium exchanged, washed, calcined in air at 538° C. for 3 hours, and then steamed for 16.5 hours at 538° C. in 100% steam. The steamed catalyst was then twice extracted with two normal nitric acid at 75° C. for 1 hour, washed and recalcined at 538° C. for 1 hour.

The above catalyst was then evaluated for methanol conversion to olefins and compared with similar catalysts which either were not treated in accordance with the process of this invention or which had different binders. In each case, the zeolite employed was ZSM-5. The results are shown in the following table.

TABLE 1

Effect of steaming and Acid-Extraction on Cycle Length for Methanol Conversion to Olefins

| Catalyst | A | B | C | D | E |
|---|---|---|---|---|---|
| Catalyst Characteristics | | | | | |
| Binder | $Al_2O_3$ | $Al_2O_3$ | $SiO_2$ | $Al_2O_3$ | $SiO_2$ |
| Steamed | No | Yes | Yes | Yes | Yes |
| Acid-Extracted | No | No | No | No | Yes |
| Alpha Value | 340 | 6 | 12 | 24 | 18 |
| Methanol-to-Olefins (MTO) Run Conditions | | | | | |
| Pressure (psig) | 0 | 0 | 0 | 0 | 0 |
| Temperatures (°F.) | 923 | 890 | 915 | 876 | 876 |
| WHSV | 2.8 | 2.7 | 2.9 | 2.9 | 3.0 |
| Results | | | | | |
| Ave. C2–C5 olefins Select. (wt % of HC) | 39 | 72 | 76 | 64 | 70 |
| Days to Methanol Breakthrough | 4 | 18 | 19 | 20 | 33 |
| Coke on feed (wt percent) | 0.165 | 0.034 | 0.032 | 0.039 | 0.014 |

As can be seen from the above table, Catalyst A which had an alumina binder and was not subjected to steaming and acid-extraction had the highest alpha value but had the worse stability (Days to Methanol Breakthrough 4). When the alumina catalyst (B) was subjected to steaming its "Days to Methanol Breakthrough" increased to 18. When a silica binder was used Catalyst (C) which was merely steamed but not acid extracted, the "Days to Methanol Breakthrough" increased to 19. When an alumina binder Catalyst (D) was used which was steamed but not acid extracted, the "Days to Methanol Breakthrough" increased to 20. Catalyst E represents the catalyst prepared in accordance with this invention (Example 1) and as can be seen it had the longest "Days to Methanol Breakthrough", i.e., the greatest stability.

Quite obviously, a catalyst which has an alumina binder cannot be subjected to acid-extraction since the acid would remove the alumina. Therefore, it is not possible to prepare an alumina-bound ZSM-5 which has been both steamed and acid extracted since the acid would attack the alumina.

The above table also clearly shows that coke on feed was the lowest for the catalyst prepared in accordance with the process of this invention (Catalyst E).

What is claimed is:

1. In the process for the conversion of methanol to hydrocarbons wherein methanol is contacted at elevated temperatures over a zeolite catalyst characterized by a silica-to-alumina ratio of at least 12 and a Constraint Index within the approximate range of 1 to 12, the improvement which comprises extruding said zeolite with silica and thereafter subjecting the extruded zeolite to steaming at a temperature of from 400° C. to 600° C. for 2 to 100 hours and acid-extraction.

2. The method of claim 1 wherein said zeolite is selected from the group consisting of ZSM-5, ZSM-11, ZSM-12, ZSM-23, ZSM-35, ZSM-38, and ZSM-48.

3. The process of claim 2 wherein the zeolite is ZSM-5.

4. The process of claim 2 wherein the zeolite is ZSM-11.

5. The process of claim 2 wherein the zeolite is ZSM-12.

6. The process of claim 2 wherein the zeolite is ZSM-23.

7. The process of claim 2 wherein the zeolite is ZSM-35.

8. The process of claim 2 wherein the zeolite is ZSM-38.

9. The process of claim 2 wherein the zeolite is ZSM-48.

* * * * *